(12) United States Patent
Kim

(10) Patent No.: US 6,632,245 B2
(45) Date of Patent: Oct. 14, 2003

(54) ANTERIOR CRUCIATE LIGAMENT RECONSTRUCTION HAMSTRING TENDON FIXATION SYSTEM

(76) Inventor: Andrew C. Kim, 30213 Del Ray Rd., Temecula, CA (US) 92591

( * ) Notice: Subject to any disclaimer, the term of this patent is extended or adjusted under 35 U.S.C. 154(b) by 0 days.

(21) Appl. No.: 09/961,509

(22) Filed: Sep. 21, 2001

(65) Prior Publication Data

US 2002/0007182 A1 Jan. 17, 2002

Related U.S. Application Data

(62) Division of application No. 09/136,268, filed on Aug. 19, 1998, now Pat. No. 6,355,066.

(51) Int. Cl.[7] .................................................. A61F 2/08
(52) U.S. Cl. ...................... 623/13.14; 606/72; 606/232
(58) Field of Search ..................... 623/13.14, 13.11, 623/13.13; 606/72, 73, 232

(56) References Cited

U.S. PATENT DOCUMENTS 2,490,364 A  *  12/1949  Livingston
5,464,427 A  *  11/1995  Curtis et al. ................. 606/232
5,713,900 A  *   2/1998  Benzel et al. ................. 606/61
5,720,753 A  *   2/1998  Sander et al. ................ 606/104
5,961,520 A  *  10/1999  Beck, Jr. et al. ............... 606/72
5,968,078 A  *  10/1999  Grotz .......................... 606/232
6,355,066 B1 *   3/2002  Kim ......................... 623/13.14

* cited by examiner

*Primary Examiner*—Bruce Snow
(74) *Attorney, Agent, or Firm*—Freling Baker

(57) ABSTRACT

A system for securing a tendon to a bore hole surface in a femur and a tibia, the system including a bone anchor having a flexible body with a distal end having an aperture to receive the tendon, and two legs forming a concave relief extending from the aperture to a split end, with the concave relief forcing the tendon into direct contact with the femur bore hole surface. An anchor insertion instrument is used to insert the anchor into the femur bore hole, the instrument having a pair of spaced apart pins to hold the bone anchor. A tibia fixation device joins the tendon to the tibia bore hole and has a generally cylindrical body with an open proximal end and at least two rounded legs formed by at least two slits extending from a distal end. At least one opening is located adjacent to the open proximal end for receiving the tendon. A clamping screw and spiked washer are used to lock the tibia fixation device and tendons into the tibia bore hole.

15 Claims, 6 Drawing Sheets

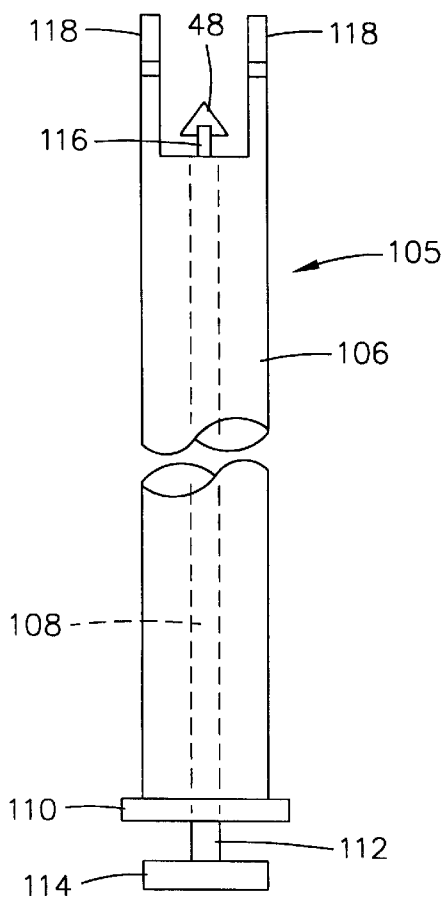
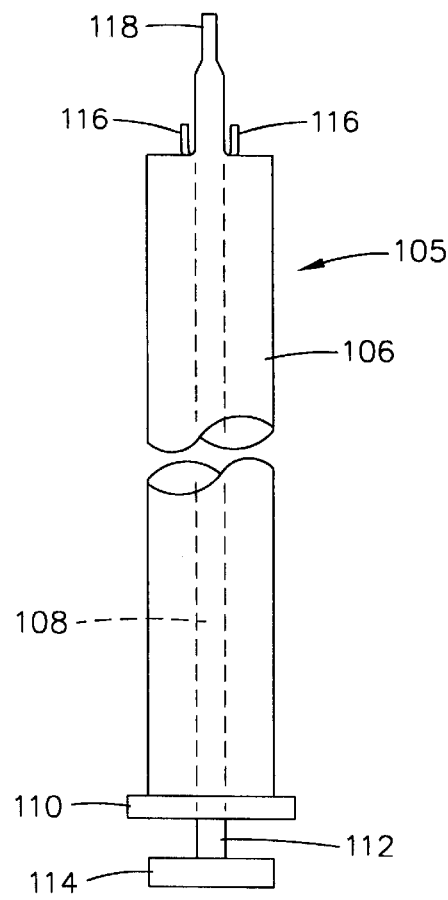
FIG. 15     FIG. 15A
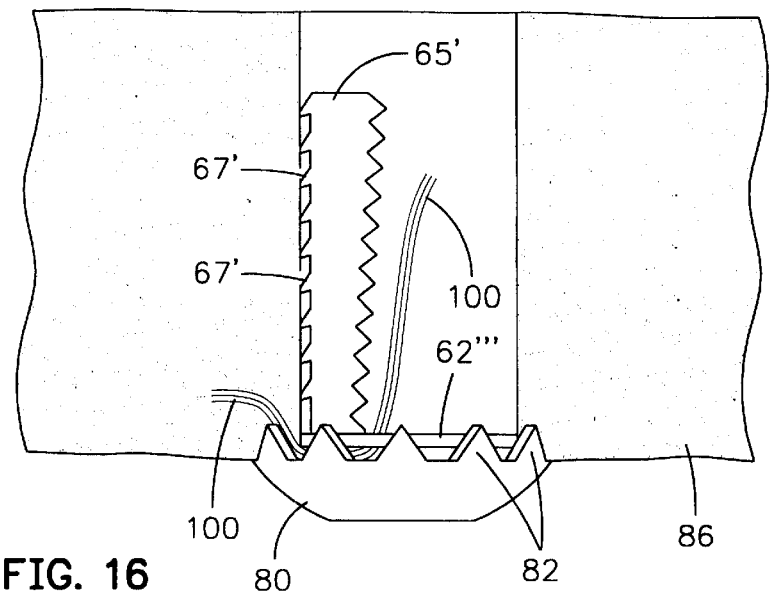
FIG. 16

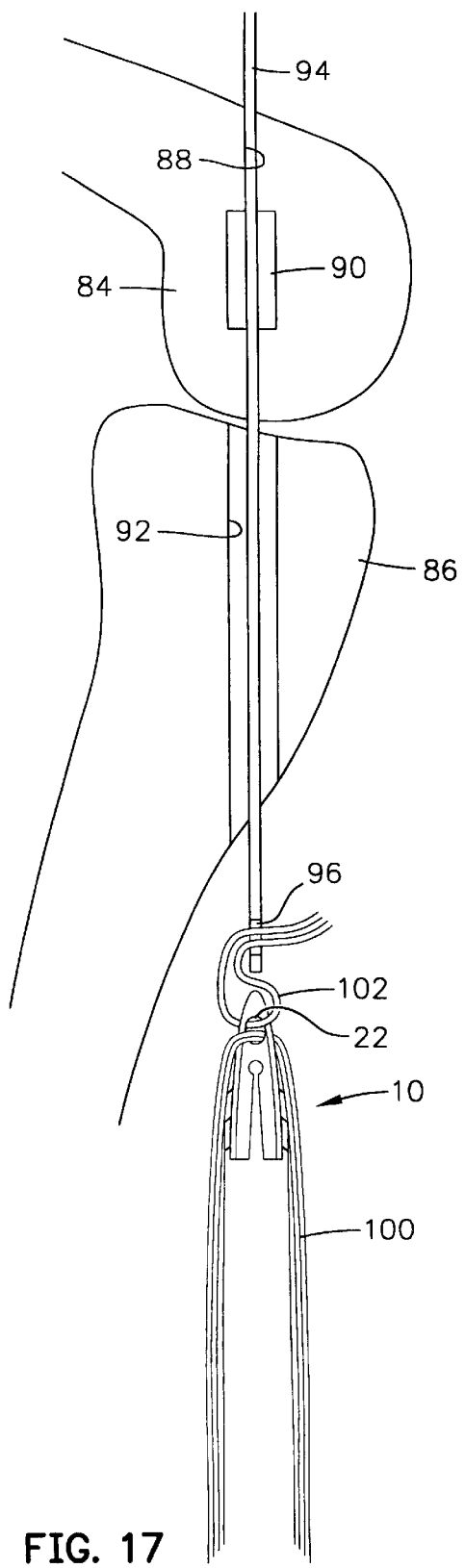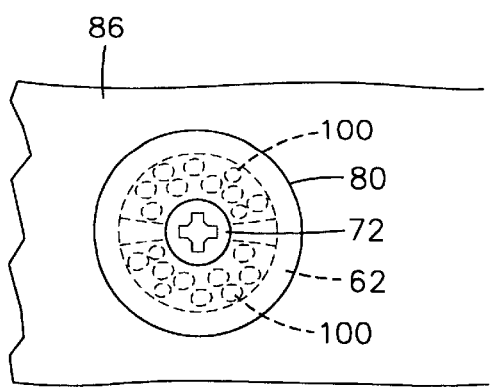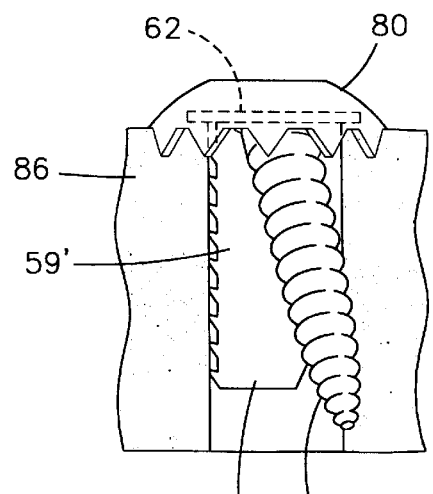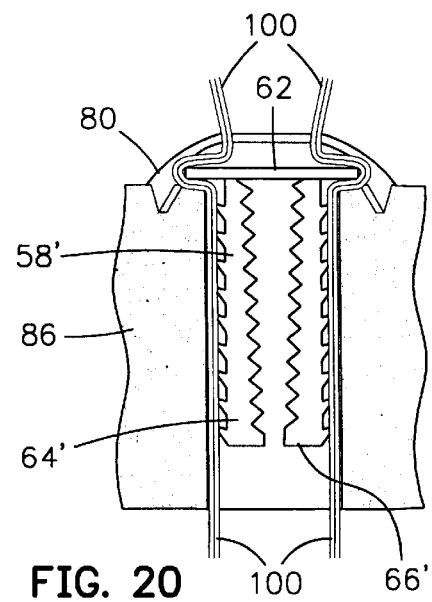
FIG. 17
FIG. 18
FIG. 19
FIG. 20

ANTERIOR CRUCIATE LIGAMENT RECONSTRUCTION HAMSTRING TENDON FIXATION SYSTEM

This application is a divisional of U.S. application Ser. No. 09/136,268 filed Aug. 19, 1998, now U.S. Pat. No. 6,355,066.

BACKGROUND OF THE INVENTION

The present invention relates to a ligament fixation system and pertains particularly to an anterior cruciate ligament reconstruction hamstring tendon fixation system.

Anterior cruciate ligament reconstruction with the use of hamstring tendon graft is becoming more popular with its benefit of lower morbidity compared to the patella bone-tendon-bone graft technique. The hamstring tendon graft technique involves the formation of tunnels in the femur and the tibia and the anchoring of tendons or ligaments in these bone tunnels. The main obstacle to the hamstring technique has been the achievement of a secure and fast fixation of the tendon into the bone tunnels. Another problem is the morbidity associated with transplanting the hamstring ligament material.

Many attempts have been made in the past to provide a suitable anchor for anchoring the hamstring tendon in the bone tunnel. None of these past attempts have been satisfactory. They have failed to overcome the aforementioned problems. Accordingly, a simple and effective anchor design that secures the tendon in the bone tunnel and decreases morbidity rates of transplanted ligament is desired.

The present invention is a system devised for an endoscopic operation to provide a simple and speedy way for securing the fixation of the tendons into the femoral and tibial tunnels and to decrease morbidity rates of the transplanted tendons or ligaments.

SUMMARY AND OBJECTS OF THE INVENTION

It is the primary object of the present invention to provide a simple and effective means for securing the fixation of tendons into femoral and tibial tunnels and to improve the survivability of the transplanted tendons.

In accordance with a primary aspect of the present invention, a femoral fixation apparatus is provided which has a somewhat bullet-shape with a threading aperture to receive tendons or ligaments and a suture. The device has an elongated slot forming resilient wings or legs having retaining burrs or ridges for retaining the anchor in a bone tunnel. The trailing sides of the anchor are relieved with a concave configuration for accommodating tendons along the sides of the anchor to engage the tendons with the bore hole surface.

Another aspect of the invention includes a tibia fixation or anchoring apparatus which comprises a generally cylindrical body having an open proximal end and two rounded legs formed by two slits extending from a distal end, and at least one opening adjacent to the open proximal end for inserting the tendon or ligament therein.

BRIEF DESCRIPTION OF THE DRAWINGS

The above and other objects and advantages of the present invention will become apparent from the following description and the accompanying drawings wherein:

FIG. 9B is a somewhat perspective view of the tibia anchor of FIG. 9A, showing details of threads and the like;

FIG. 15 is a front elevation view of a first embodiment of a femoral anchor insertion instrument;

FIG. 15A is a side elevation view of the embodiment of FIG. 15;

FIG. 16 is a side elevation view illustrating the initial stages of the installation of a femoral anchor, tendons and the washer of FIG. 14;

FIG. 17 is a side elevation view of the femoral anchor of FIG. 1, tendons, and a suture being pulled into the tibia and femur bone holes;

FIG. 18 is a plan view illustrating a tibia anchor, tendons, and a screw installed in a bore hole in a bone;

FIG. 19 is a side elevation view illustrating a tibia anchor, a screw, and an umbrella-shaped washer installed in a bore hole in a bone;

FIG. 20 is a view like FIG. 19, illustrating the anchor of FIG. 10, tendons and the washer of FIG. 14 in a bore hole in a bone;

DETAILED DESCRIPTION OF THE PREFERRED EMBODIMENTS

Figure 1:
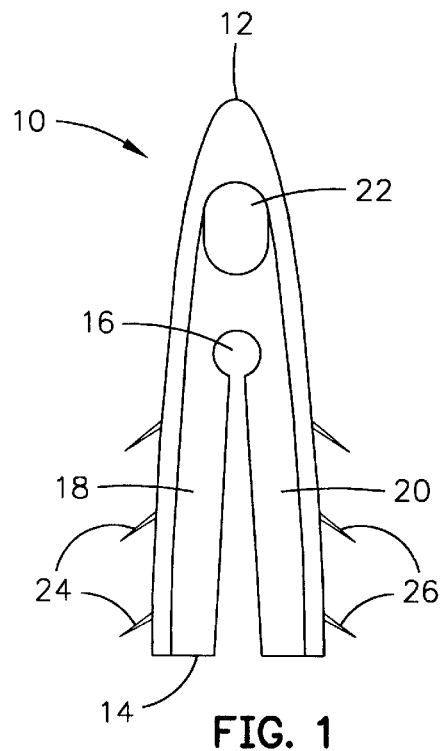
FIG. 1 is a front elevation view of a first embodiment of a femoral anchor.
Figure 2:
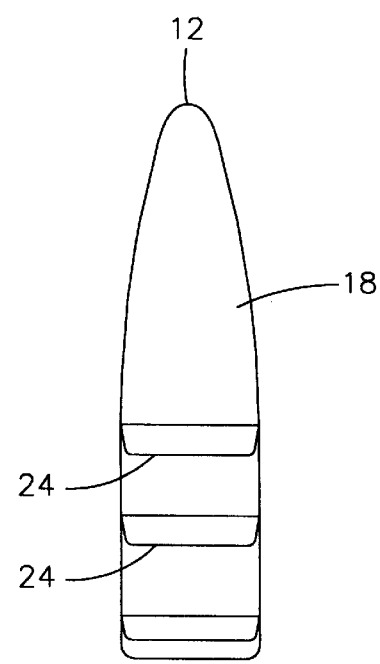
FIG. 2 is a side elevation view of the femoral anchor of FIG. 1.
Figure 3:
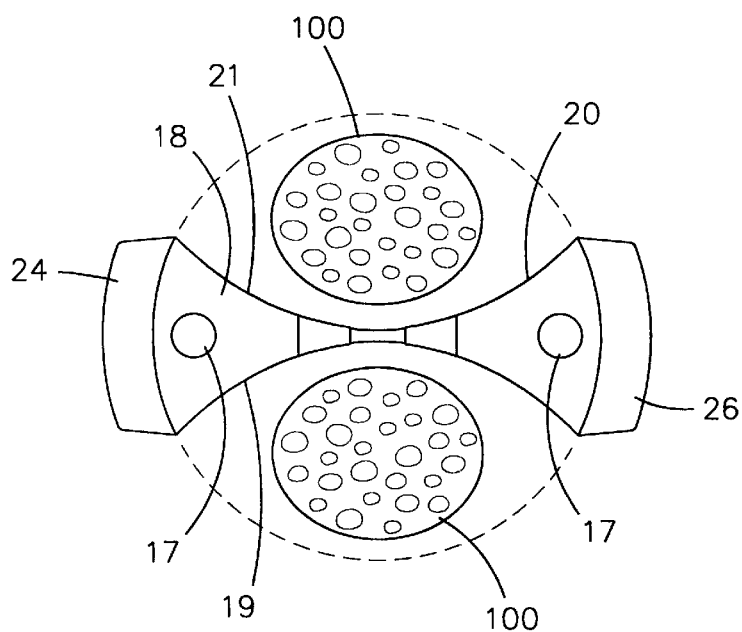
FIG. 3 is a bottom end view of the femoral anchor of FIG. 1, with tendons positioned thereon.

Referring to FIGS. 1–3 of the drawings, a femoral anchor in accordance with one embodiment of the invention is illustrated and designated generally by the numeral 10. The anchor, as seen in FIG. 1, has a generally bullet-like upper configuration tapering to a rounded tip or point 12 at an upper or forward end with curved sides extending down to a bottom or back end 14 with a slit extending from the bottom end upward to an opening 16 forming a pair of legs or wings 18 and 20. An eye or aperture 22 is formed toward the upper or forward end of the anchor for threading ligaments 100 through. The outer facing sides of the surfaces of the legs are formed with a number of burrs or anchoring ridges or barbs 24 and 26.

As shown in FIGS. 1 and 3, the sides of the anchor are scalloped inward beginning at the aperture 22 to form concave recesses to accommodate ligaments 100 lying along the sides of the two legs 18 and 20, as shown in FIG. 3. The legs 18 and 20 are shaped to have a substantially triangular cross-section, comprising a base, two sides, and an apex, with the base forming an outer convex surface, and the sides of the triangles forming the concave recesses 19 and 21. Because there is more surface area on the two sides and apex of the legs 18 and 20 compared to the base, the surface tension difference will tend to push the legs outward, against the bone, and thus lodge in the bone more readily. In one embodiment, the legs are formed to have a pre-bias outward so that the outer surfaces are biased into engagement with the tunnel walls.

The scalloped or concaved surfaces 19 and 21 provide space along the opposite sides of the body of the anchor for receiving and accommodating the ligaments 100 which are threaded through the eye or aperture 22 and trail behind the anchor as it is pulled, or otherwise inserted, into the tunnels. Once placed in the bone tunnel, the ligaments 100 are pressed against the bone tunnel surface by the concave leg surfaces 19 and 21, thus decreasing transplant morbidity and recovery time for the patient. Additionally, the pressure of the ligaments against the sides of the legs pushes the legs outward, against the tunnel wall.

Figure 4:
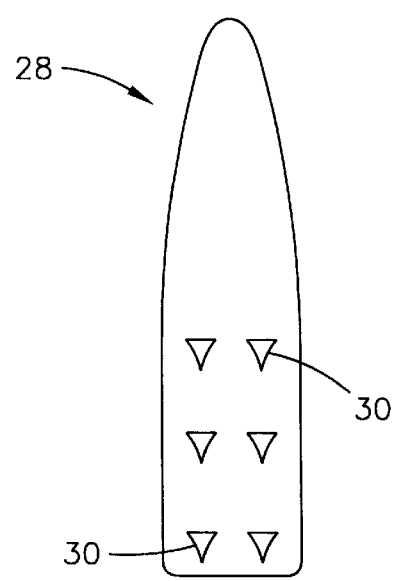
FIG. 4 is a side elevation view of an alternate embodiment of a femoral anchor.
Figure 5:
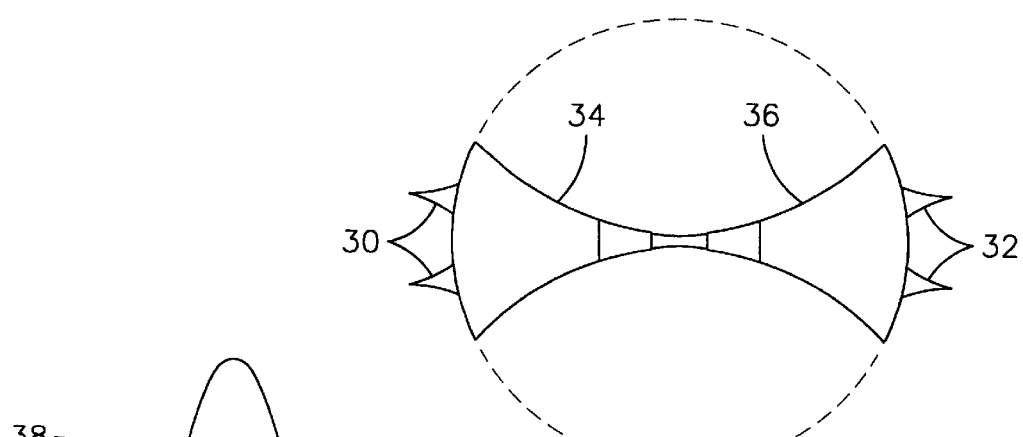
FIG. 5 is a bottom end view of the embodiment of FIG. 4.

Referring to FIG. 4 of the drawings, an anchoring device designated generally by the numeral 28 is illustrated and is constructed substantially the same as of the FIG. 1 embodiment. However, this embodiment is provided with spike-like anchoring barbs 30 on the legs 34 and 36. The anchors 10 and 28 can be made of any one or a combination of materials, including metals, plastic or bioabsorbable material.

For easy insertion of the anchor 10 into a bone tunnel, the legs 18 and 20 may be compressed and held by a bifurcate end 118 of an insertion instrument 105 (FIGS. 15 and 15A) which may also be used as an impactor.

Figure 6:
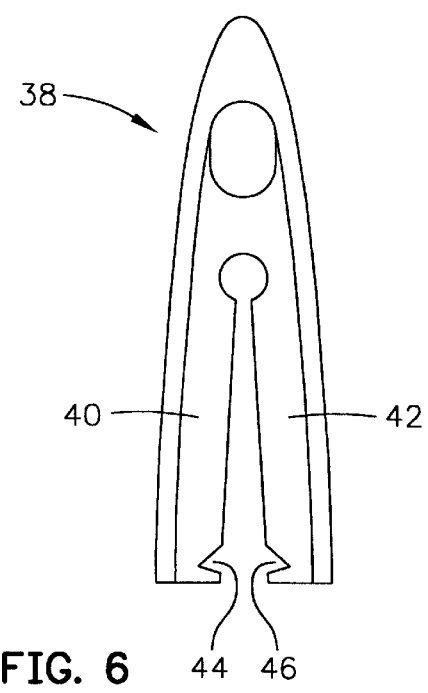
FIG. 6 is a front elevation view of an alternate embodiment femoral anchor, wherein the slits between the two legs are formed with notches to accommodate a wedge.
Figure 7:
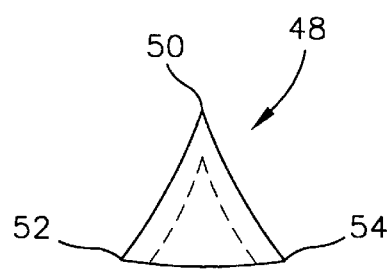
FIG. 7 is a front elevation view of a wedge for the embodiment of FIG. 6.
Figure 8:
FIG. 8 is a side elevation view of the wedge of FIG. 7.

Once the anchoring device is inserted into a bore hole, a wedge 48 can be inserted and lodged between the anchor's legs. Referring to FIG. 6, an anchor device designated generally at 38 is illustrated and constructed essentially the same as that of FIGS. 1 and 2. The legs 40 and 42 are formed with notches 44 and 46 at their apex, or lower inner edges thereof. These notches are designed to accommodate a wedge designated generally at 48, as illustrated in FIGS. 7 and 8. The wedge has a generally triangular shape, as shown in FIG. 7, with an upper pointed end 50 with grooved surfaces extending down to edges 52 and 54 which engage and retain the wedge in the notches 44 and 46 between the legs 40 and 42. The wedge serves to force or spread the legs outward and further force the anchoring thereof tightly in the tunnels in the femur. The insertion instrument 105 has a plunger 112 with a forked end 116 that pinches the wedge 48 to hold, and guide it for insertion and placement against the notches 44 and 46.

Referring to FIG. 3, the concave surfaces 19 and 21 at the sides of the substantially triangular legs receive the tendons or ligaments 100 in the front and back of the convex surfaces. The fixation spikes or barbs 24 and 26 on the outer convex surfaces of the legs 18 and 20 engage the bone directly and any force attempting to pull the device backward will cause the legs 18 and 20 to further spread and the barbs to dig deeper into the bone, therefore, more securely anchoring it into place. The concave surfaces of the anchoring device 10 also positions and forces the tendons 100 into direct contact with the inner surface of the bone resulting in a faster growth to and securing thereto.

Figure 9A:
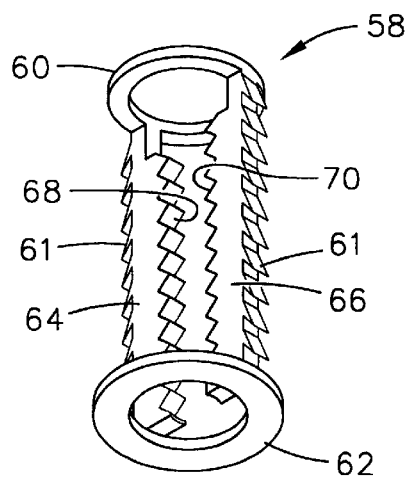
FIG. 9A is a perspective view of a tibia anchor.
Figure 9B:
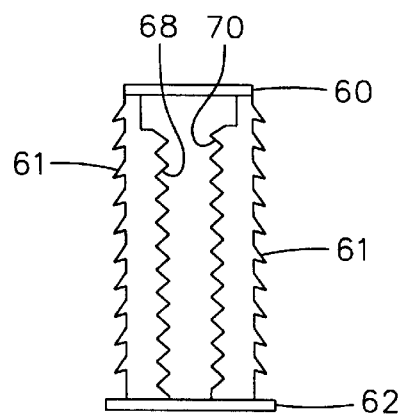

Referring to FIGS. 9A and 9B, a tibia fixation device, or anchor, or cage, designated by the numeral 58 is illustrated and comprises an upper or forward ring 60 and a proximal or bottom ring 62 connected together by a pair of elongated longitudinally extending side legs, or rails 64 and 66. Bottom ring 62 is common as to some of the alternative embodiments of the tibia anchor, hereinafter discussed and designated 58', 59, 59' and 120. The side legs 64 and 66 are provided with threads 68 and 70 on the inner surfaces thereof for engagement by screw 72. The outer surfaces of the legs have anchoring ridges or barbs 61 to better grip the bone in the tunnel. The inner or upper ring 60 is of a smaller diameter than that of the outer ring 62 and is sized to fit into the tunnel, or bore hole, in the tibia. The upper ends of the legs 64 and 66 are notched as illustrated, adjacent to the ring 60. The outer ring 62 is about 2 mm larger in diameter than the inner ring and will act as a collar on the surface of the tibia bone.

Figure 13:
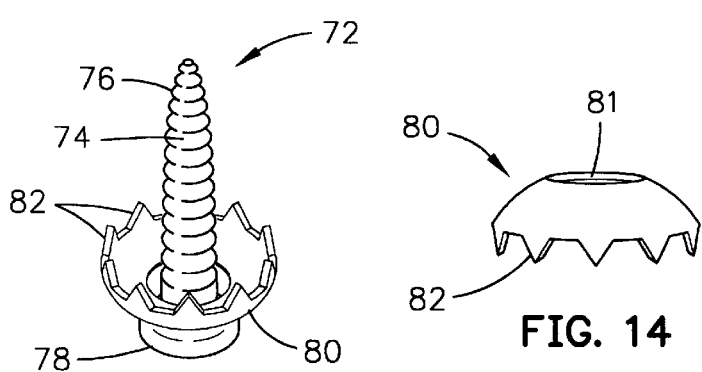
FIG. 13 is a perspective view of the fixation screw and washer for the tibia anchors.
Figure 14:
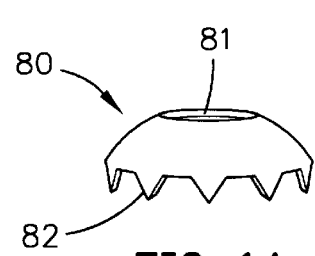
FIG. 14 is a side elevation view of the washer shown in FIG. 13.
Figure 14A:
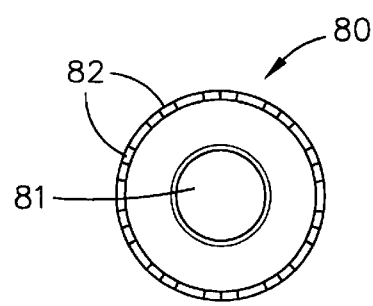
FIG. 14A is a plan view of the washer shown in FIG. 13.

FIG. 13 shows an elongated tibia anchor screw designated generally at 72, having a removable washer 80 positioned thereon. The screw is formed of an elongated shank 74 having threads 76 extending along the length of the outer surface thereof for threadably engaging threads on any one of the tibia anchors herein described. The shank may be slightly tapered, as shown, so that it may affect a slight expansion of the tibia anchor as it is inserted therein. The screw is preferably in the form of a 6.5 cancellous screw (A-0). An umbrella shaped washer 80, shown in FIGS. 14 and 14a, may be received on the screw and may preferably include spikes 82 for engaging and anchoring the tendons to or into the surface of the tibia. Washer 80 is umbrella shaped with spikes extending from a bottom surface, and containing an aperture 81 for receiving the screw 72. The washer acts like a clamp to cover the tendons 100 and bottom ring 62 to lock the tendons against the tibia bone. Both the screw and washer can be used with any one of the tibia anchors herein described.

Figure 10:
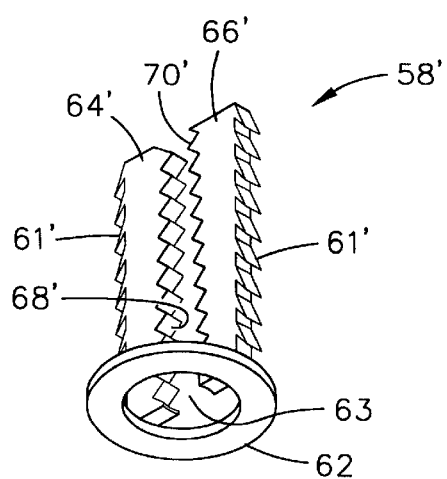
FIG. 10 is a perspective view of an alternative embodiment of a tibia anchor.

FIG. 10 illustrates an alternative embodiment of tibia anchor, or cage 58'. Tibia anchor 58' comprises bottom ring 62 having a pair of longitudinally extending side legs, or prongs 64' and 66'. The legs are provided with threads 68' on the inner surfaces thereof for an engagement by preferred anchor screw 72. The outer surfaces of the legs have anchoring ridges, threads, or barbs 61' to grip the bone. Legs, or prongs 64' and 66' increase in thickness (radially) from the attachment point on the ring to their ends. This forms channel 63 having a decreasing width, which forces legs 64' and 66' outwards into engagement with the bone tunnel when screw 72 is threaded into the channel. Preferably, tendon 100 may extend along the outer surfaces of the legs, or prongs of any one of the tibia anchors, so that when screw 72 is threaded into channel 63, the tendons are forced against the bone tunnel surface, shown in FIG. 20. Legs 64' and 66' taper along their length, as shown in FIG. 12a, with their widest dimension (circumferential) at ring 62 attachment point. Wide section 71 below the ring resists twisting when screw 72 is installed. Narrower end portion 73 allows for easier installation of the tibia anchor into the bone tunnel. Legs, or prongs 64' and 66' also flex relative to the ring resulting in a hinge-like connection. This flexible hinge-like effect between the ring and the legs allows for easier installation into angled bone tunnels. Preferably, all tibia anchor legs flex relative to the ring.

Figure 11:
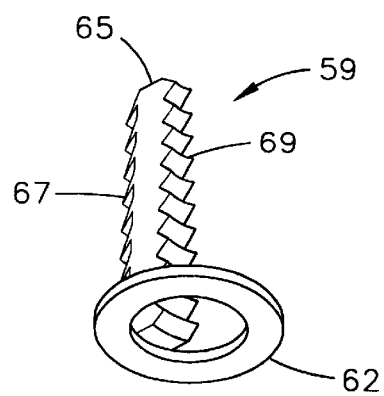
FIG. 11 is a perspective view of another embodiment of a tibia anchor.

Referring to FIG. 11 another embodiment of a tibia anchor is illustrated and designated generally at 59. Tibia anchor 59 has a common ring 62, as in the prior embodiment and has a single elongated longitudinally extending side rail 65. The side rail has threads 69 on the inner surface thereof. The outer surface of the rail has a number of anchoring ridges, threads, or barbs 67 to lodge in the bone. Ring 62 acts as a collar on the surface of the tibia bone as shown in FIG. 16. The side rail 65 tapers along its length, as shown in FIG. 12a, with its widest dimension circumferentially at the ring attachment point. Wide section 71 immediately below the ring resists twisting once screw 72 is installed. Narrower end portion 73 allows for easier installation of tibia anchor 59 into the bone tunnel. Rail 65 also flexes relative to ring 62 for easier installation into angled bone tunnels.

Figure 12:
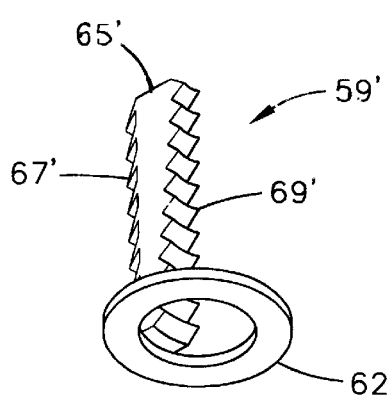
FIG. 12 is a perspective view of a further embodiment of a tibia anchor.
Figure 12A:
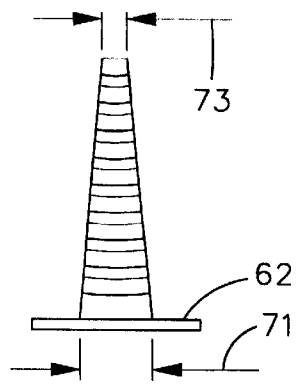
FIG. 12A is a side elevation view of the tibia anchors of FIGS. 12 and 10.

FIG. 12 illustrates a further embodiment of a tibia anchor. Tibia anchor 59' has a ring 62 like prior embodiments, and has a single elongated longitudinally extending side rail 65'. The side rail has threads 69' on the inner surface thereof. The outer surface of the rail has a number of anchoring ridges, threads or barbs 67' to lodge in the bone. Ring 62 acts as a collar on the surface of the tibia bone as shown in FIG. 16. Like tibia anchor 58', the rail of tibia anchor 59' increases in thickness from its attachment on the ring 62 to its end. The rail 65' also tapers along its length, as shown in FIG. 12a, with its widest dimension circumferentially at the ring attachment point. Wide section 71 immediately below the ring resists twisting once screw 72 is installed. Narrower end portion 73 allows for easier installation of tibia anchor 59' into the bone tunnel. Rail 65' also flexes relative to ring 62 for easier installation into angled bone tunnels.

Figure 21:
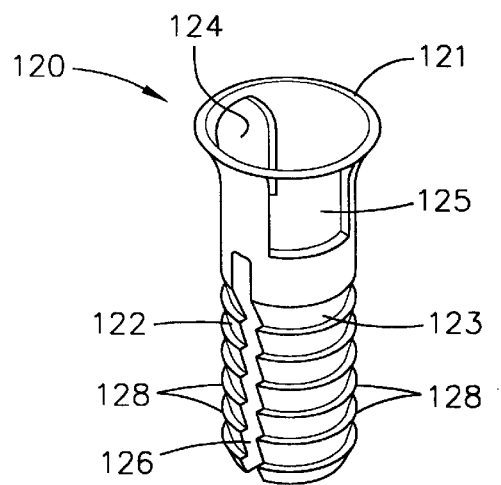
FIG. 21 is a perspective view of yet another embodiment of a tibia anchor.
Figure 22:
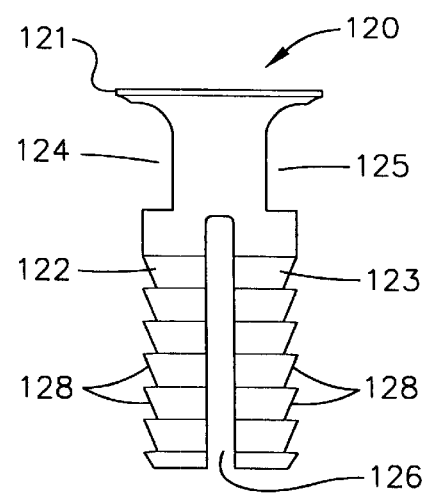
FIG. 22 is a side elevation view of the tibia anchor of FIG. 21.
Figure 23:
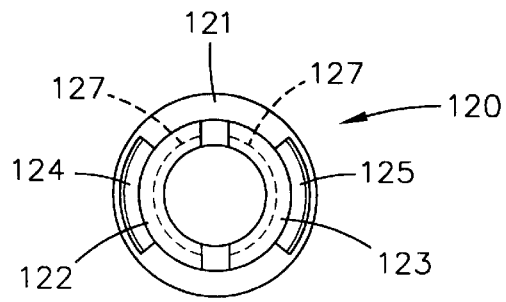
FIG. 23 is a bottom plan view of the tibia anchor of FIG. 21.
Figure 24:
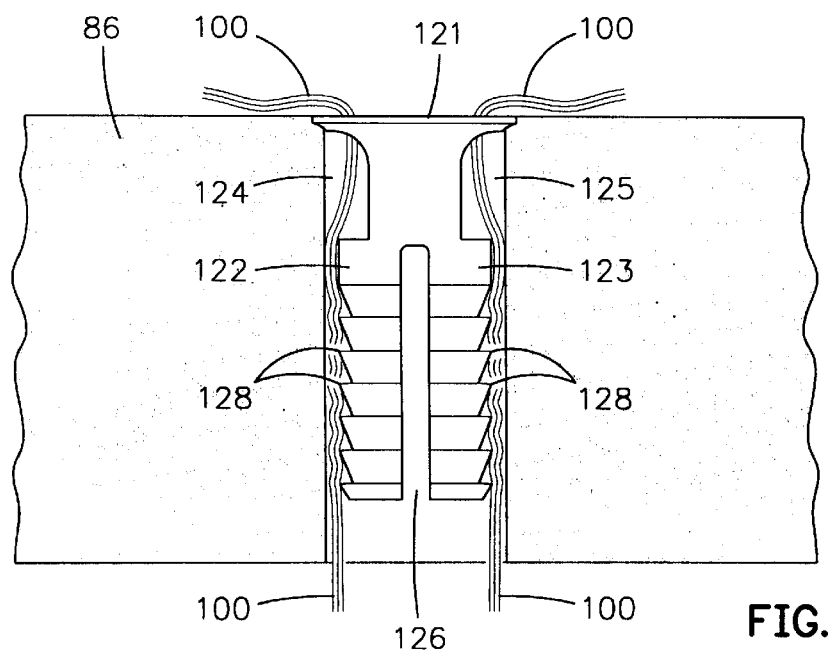
FIG. 24 is a side elevation view illustrating the tibia anchor of FIG. 21, and tendons in a bore hole in a bone.

Referring to FIGS. 21, 22 and 23, a preferred embodiment tibia anchor, or cage designated by the numeral 120 is illustrated and comprises an upper cylindrical surface 121 forming an open end, with a pair of elongated longitudinally extending legs, or rails 122 and 123 formed by a slit, or slits 126. Preferably, the upper cylindrical area has a slightly larger diameter than the diameter of the legs, so that the upper surface 121 lodges against the opening of the bore hole, as shown in FIG. 24. Below the upper cylindrical surface is a somewhat cone shaped area having two openings 124 and 125 through which tendons 100 pass. As shown in FIGS. 21 and 22, the generally square openings are somewhat angled from the vertical plane, which allows the tendons to be easily placed therein. The legs 122 and 123 are provided with threads 127 on the inner surfaces thereof for engagement with screw 72, shown in FIG. 23. In some embodiments, the legs are flexible and radially expandable, and increase in thickness from below the openings 124 and 125 to their ends. When screw 72 is installed, the screw forces the thicker sections into engagement with the tendons 100 and the bore hole wall, firmly locking the tendons in the bore hole. The outer surfaces of the legs have anchoring ridges or barbs, or burrs 128 to engage the tendons and the bone tunnel surface, as shown in FIG. 24. The outer surface of the legs is generally rounded, forming a somewhat cylindrical surface. This improves engagement with the tendons 100, tunnel walls, and screw 72, as surface area is increased, and the outer surface of the legs matches the curved surface of the bone tunnel, or bore hole. As an alternative embodiment, all of the tibia anchors described herein can have their legs, or rails curved, or rounded in a like manner.

Referring to FIG. 24, the tibia anchor 120 is positioned in a tibia bone tunnel with tendons 100 trapped between the legs 122 and 123 and the bone surface. Screw 72 (not shown) is threaded through the center of the tibia anchor, and engages with tibia anchor threads 127 (not shown) and forces the legs 122 and 123 outward, trapping the tendons against the bone tunnel surface and also engaging the leg barbs 128 against the bone tunnel surface. Washer 80 can be placed over the upper cylindrical surface 121, clamping tendons 100 against the bone surface. All the tibia anchors, or cages herein described, and washer 80 can be made of any one or a combination of materials, including metals, plastic or bioabsorbable material.

Now referring to FIG. 17, a femur 84 is illustrated in position to join a tibia 86. The tibia is formed with a small thru-bore 92 and the femur is formed with a tunnel 90. The femur bore 88 is aligned with and co-axial with a bore or tunnel 92 formed in and extending through the tibia 86. An elongated pin or needle 94 having an eye 96 extends through the bore with the eye 96 positioned below the opening into the tunnel 92 of the tibia. In operation, a femoral anchor, such as 10, is selected and ligaments, or tendons 100 are threaded through the eye 22 thereof and extend down along the side of the legs, as shown for example in FIG. 3, or alternatively down the outside of the legs, as shown in FIG. 17.

A suture 102 is threaded through the eye 22 and through eye 96 of the needle or pin 94. The pin is then pulled upward until the fixation anchor 10 is positioned in the tunnel 90. The legs of the femoral anchor may be compressed to facilitate the movement of the anchor into the tunnel 90. This can be accomplished by attaching the anchor 10 at indentation points 17, to fork 118 on insertion instrument 105. Once positioned in the tunnel 90 the tendons 100 are pulled downward, thus forcing the legs of the anchor outward and the burrs 24 of the anchor tighter into the surfaces of the bone in the tunnel 90. Alternatively, the anchor 10 can be installed by use of an insertion tool 105 without the use of a needle 94.

Once the tendons 100 are well anchored into place, the pin 94 and suture 102 may be removed and any one of the herein described tibia anchors can be threaded onto the tendons 100. Once the tibia anchor is in place in tunnel 92, the tendons are properly tensioned by a tension device (not shown) and the screw 72 and washer 80 put in place and secured to clamp the tendons 100 in place in the tunnel and to the bone. The tension device will read the most optimum tension of tendons 100, and then screw 72, with or without washer 80, is inserted and secured. This properly secures the tendons at both ends in the respective tunnels of the respective femur and tibia.

FIGS. 15 and 15A of the drawings show an insertion instrument 105, with FIG. 15A showing the instrument rotated ninety degrees. Insertion instrument 105 has an elongated hollow or tubular shaft 106 with a handle 110 at one end, and a bifurcated end, or a pair of spaced apart pins 118 at the other end. Plunger 112 is slidably mounted within the hollow shaft. The plunger has a handle 114 on one end, and a forked end 116 on the other end, connected by rod 108. Bifurcated end 118 is disposed at about ninety degrees to forked end 116 of the plunger. The forked end can engage and grip an optional wedge 48 for insertion between the legs of a femoral anchor. Bifurcated end 118 engages holes or sockets 17 in the legs 18 and 20 of the femoral anchor 10 for holding them in a retracted, or compressed position, to facilitate insertion of the femoral anchor into a bore hole. The femoral anchor may be pushed into the tunnel. The insertion instrument 105 can be made of any one or a combination of materials, including metals, aluminum or titanium alloys, or plastic.

Referring to FIG. 16, a tibia anchor 59' is shown inserted in a tunnel with ring 62 is shown approximately flush with the surface of bone 86. Rail 65' engages the bone surface with anchoring barbs 67'. Tendon 100 is threaded through the bore hole and over the top of the ring and out under washer 80. Circular washer 80 having a plurality of spikes 82 is secured by a screw (not shown) to the bone surface, clamping tendons 100 against the bone. FIG. 16 shows the washer only partially lodged in the bone. The washer can be slightly larger in diameter than ring 62 so that the washer and ring are flush with each other, when completely secured into the bone by screw 72, thus securely locating the tendons 100.

FIG. 18 shows a top view of screw 72, and washer 80 inserted in a bore hole with tibia anchor 58', and tendons 100 shown in phantom. FIG. 19 shows tibia anchor 59' installed in bone 86 with washer 80 clamped to the bone by screw 72, which engages both the bone and the rail 65', fixing the tibia anchor into the bore hole.

FIG. 20 shows an alternative method of securing tendon in a tibia bone tunnel. Tendons 100 are trapped between legs 64' and 66' of tibia anchor 58' and the surface of bone tunnel 86. The tendons are routed between the bone and ring 62 and protrude through aperture 81 of circular washer 80. When screw 72 is installed through the aperture, the tendons are trapped between the screw and the aperture, the circular washer and the ring, the ring and the bone, and the legs and the bone.

While I have illustrated and described my invention by means of specific embodiments, it is to be understood that numerous changes and modifications may be made therein without departing from the spirit and the scope of the invention as shown in the appended claims.

What is claimed is:

1. A bone anchor for securing a tendon or ligament in a bore hole in a bone, comprising:
    a generally cylindrical body having an open proximal end and at least two rounded legs formed by at least two slits extending from a distal end, the legs having a threaded inner surface at least at the distal end; and
    at least one opening adjacent the open proximal end for inserting the tendon or ligament therein.

2. The bone anchor of claim 1, wherein the open proximal end has a diameter that is greater than the generally cylindrical body, so that the open proximal end lodges in an opening of the bone.

3. The bone anchor of claim 1, wherein the rounded legs increase in thickness from the open proximal end to the distal end.

4. The bone anchor of claim 1, wherein the rounded legs are radially expandable and have an inner surface with threads thereon for engaging with a screw.

5. The bone anchor of claim 1, further comprising anchoring means on the outer surface of the rounded legs, the anchoring means selected from the group consisting of burs, anchoring ridges and barbs.

6. The bone anchor of claim 1, further comprising a screw for inserting into the open proximal end for forcing the tendon or ligament against the bore hole surface, and for locking the apparatus in the bore hole.

7. A bone anchor for securing a tendon or ligament in a bore hole in a bone, comprising:
    a generally cylindrical body having an open proximal end and at least two rounded legs formed by at least two slits extending from a distal end;
    at least one opening adjacent the open proximal end for inserting the tendon or ligament therein; and
    a washer having an aperture and a plurality of spikes located about a perimeter, so that when the washier in placed over the open proximal end of the spikes clamp the tendon or ligament against a bone surface.

8. A kit for securing a tendon into a femur bone hole and a tibia bore hole, the kit comprising:
    a) a femoral bone anchor comprising:
        a flexible body having a distal end with an aperture therein to receive the tendon, the body tapering in the direction of the distal end from a split end; and
        two legs extending from adjacent the aperture and including a concave relief extending from the aperture to the split end; and
    b) a tibia fixation apparatus comprising:
        a generally cylindrical body having an open proximal end and at least two legs formed by at least two slits extending from a distal end; and
        at least one opening adjacent to the open proximal end for inserting the tendon therein.

9. The kit of claim 8, further including an anchor insertion instrument for inserting the femoral bone anchor into the femur bone hole, the anchor insertion instrument comprising:
    a shaft;
    a handle at a first end of the shaft;
    a pair of spaced apart pins at a second end of the shaft; and
    a plunger slidably mounted within the shaft, the plunger having a forked end that protrudes from the second end of the shaft, and an actuator that protrudes from the first end of the shaft, wherein the forked end and the pair of spaced apart pins are disposed at about ninety degrees relative to each other.

10. The kit of claim 9, further comprising at least one indentation on each of the femoral anchor legs at the split end, for cooperating with the pair of spaced apart pins of the anchor insertion instrument.

11. The kit of claim 8, further comprising:
    a substantially circular washer having a central aperture and a plurality of spikes positioned about a periphery; wherein the washer is placed over the tibia fixation apparatus for clamping the tendon against a bone surface.

12. The kit of claim 8, further including a screw for securing the tibia fixation apparatus into the tibia bore hole.

13. The kit of claim 8, further comprising anchoring means on an outer surface of the legs of the femoral anchor and on an outer surface of the legs of the tibia fixation apparatus, the anchoring means selected from the group consisting of burrs, anchoring ridges, and barbs.

14. The kit of claim 8, further comprising a wedge member, for engaging the femoral bone anchor legs, the wedge forcing the legs against an inner surface of the femur bore hole.

15. The wedge member of claim 14, wherein the wedge member is inserted in the bone anchor legs by an anchor insertion instrument.

* * * * *